United States Patent [19]

Roussel et al.

[11] 4,409,979

[45] Oct. 18, 1983

[54] DEVICE FOR OBSERVING AND TREATING THE EYE USING A LASER

[75] Inventors: Philippe Roussel, Thun; Franz Fankhauser; Eugen van der Zypen, both of Bern, all of Switzerland

[73] Assignee: Lasag AG, Thun, Switzerland

[21] Appl. No.: 211,207

[22] Filed: Nov. 28, 1980

[30] Foreign Application Priority Data

Nov. 28, 1979 [CH] Switzerland ............. 10570/79
Mar. 5, 1980 [FR] France ............. 80 04994

[51] Int. Cl.³ ............................................. A61B 17/36
[52] U.S. Cl. ................................ 128/303.1; 128/395; 219/121 L
[58] Field of Search ............. 128/303.1, 395–396; 350/20, 33; 331/94.5, DIG. 1; 219/121 L, 121 LM; 372/6

[56] References Cited

U.S. PATENT DOCUMENTS

| | | | |
|---|---|---|---|
| 3,096,767 | 7/1963 | Gresser et al. | 128/395 |
| 3,315,680 | 4/1967 | Silbertrust et al. | 128/395 |
| 3,348,547 | 10/1967 | Kavanagh | 128/395 |
| 3,417,754 | 12/1968 | Smart | 128/395 |
| 3,452,296 | 6/1969 | Lockenvitz et al. | 331/94.5 |
| 3,456,651 | 7/1969 | Smart | 128/303.1 |
| 3,487,835 | 1/1970 | Koester et al. | 128/303.1 |
| 3,547,125 | 12/1970 | Tagnon | 128/303.1 |
| 3,703,176 | 11/1972 | Vassiliadis et al. | 128/395 |
| 3,710,798 | 1/1973 | Bredemeier | 219/121 L X |
| 3,769,963 | 11/1973 | Goldman et al. | 128/395 X |
| 3,828,788 | 8/1974 | Krasnov et al. | 128/303.1 |
| 3,850,527 | 11/1974 | Winthrop et al. | 356/129 |
| 3,906,953 | 9/1975 | Wallace et al. | 128/303.1 |
| 3,930,504 | 1/1976 | De Laforcade | 128/303.1 |
| 4,069,823 | 1/1978 | Isakov et al. | 128/303.1 |
| 4,135,791 | 1/1979 | Govignon | 351/7 |
| 4,164,222 | 8/1979 | Prokhorov et al. | 128/303.1 |
| 4,289,378 | 9/1981 | Remy et al. | 350/174 |

FOREIGN PATENT DOCUMENTS

| | | |
|---|---|---|
| 7256 | 1/1980 | European Pat. Off. . |
| 2032394 | 8/1979 | Fed. Rep. of Germany ... 128/303.1 |
| 2197614 | 2/1973 | France . |
| 2163302 | 6/1973 | France . |
| 964567 | 7/1964 | United Kingdom . |
| 1184814 | 4/1967 | United Kingdom ............. 128/395 |
| 2020846 | 11/1979 | United Kingdom . |

OTHER PUBLICATIONS

Krasnov; "Q-Switched Laser Goniopuncture"; *Arch. Ophthalmol.;* vol. 92, 7-1974, pp. 37-41.
Van Der Zypen et al.; "The Ultrastructural Features of Laser Trabeculopuncture and Cyclodialysis"; *Ophthalmologica;* 8-1979, pp. 189-200.
Bonney et al.; "Low-Energy, Q-Switched Ruby Laser Iridotomies in Macaca Mulatta", *Invest Ophtalmol. Visual Sci.,* 3-1979, pp. 278-287.

Primary Examiner—Lee S. Cohen
Assistant Examiner—Angela D. Sykes
Attorney, Agent, or Firm—Berger & Palmer

[57] ABSTRACT

A device for observing the eye in order to treat the same comprising optical elements producing optical illumination beams which issue from a light source. The beams consist of parallel rays whose axes are eccentric and parallel to the axis of the focussing lens and traverse the lens. Observation beams and illuminating beams are combined in one optical system. Beams emerging from the focussing lens or the eccentric illuminating rays exhibit a certain inclination relative to the axial observation beam.

5 Claims, 10 Drawing Figures

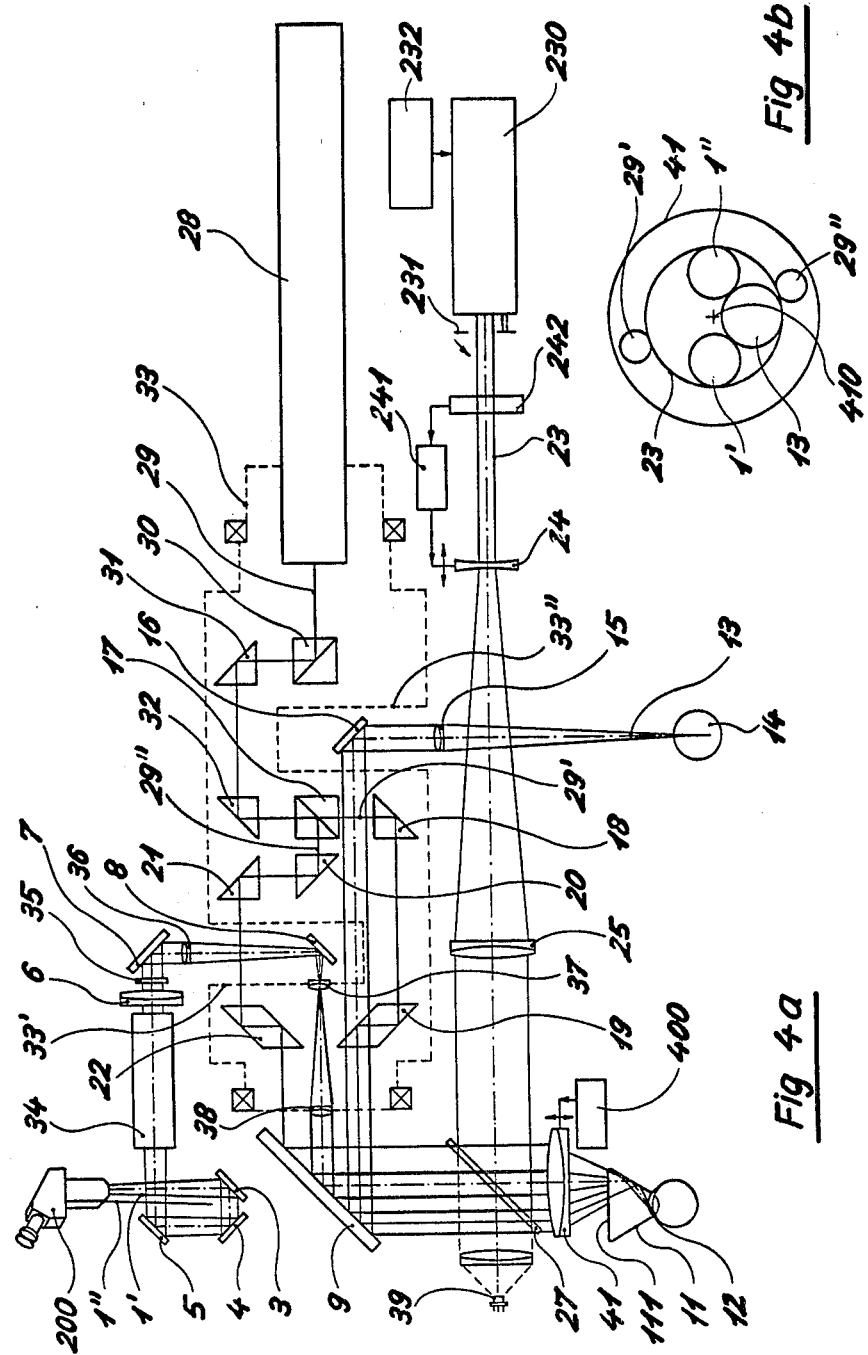

DEVICE FOR OBSERVING AND TREATING THE EYE USING A LASER

The present invention relates to a device for observing the eye in order to treat the same, comprising optical elements producing an optical beam for observing and at least one optical beam which illuminates a small region or a point within the eye, like a source of light.

Various ophthalmological instruments are known which allow detailed observation of one or more regions of the eye to diagnose a diseased eye. Most of these instruments are combined with photographic apparatus which registers the characteristic being studied by the physician.

The most popular instruments of this sort are shown, for example in the "Die ophthalmologischen Untersuchungsmethoden" by Wolfgan Straub-(Published in 1970 Ferdinand Enke Verlag Stuttgart) and in the chapter "Photography" by Helmut Riedel, pages 243 to 262 of the book: "Glaucoma, Conception of a Disease" by Klaus Heilman and Kenneth D. Richardson. In the latter reference, a first type of device for observing the anterior chamber of the eye is shown. The examination of the anterior chamber of the eye, and, to be more precise, the examination of the angle formed by the iris and the posterior face of the cornea, the irido-cornean angle may only be performed with the aid of a contact body (Goldmann type, for example) in order to prevent the total reflection of light which falls upon the transparent parts of the cornea. This contact body consists usually of a block of transparent matter (glass or plastic) and possesses an entering face, either plane or convex, a mirror as well as a concave escape surface which abuts in direct contact the anterior face of the cornea. The ophthalmologist usually manually applies and orients the contact body to the eye in order to observe the region which he wants to study.

An instrument of this first type which is used simultaneously with a contact body consists of two dimensional optical systems. One is an optical system responsible for the illumination of the observed point. An example of the first type of instrument is shown schematically in FIG. 1 where A denotes the eye of the patient, B the contact body, C the source of light, D the observing instrument and E the observer.

When one illuminates the zone or the point which one wants to study, it is important to prevent parasitic reflections which, for example, arise at the entering surface of the contact body because they might interfere with the observation. Therefore, this illumination is performed by an independent system which may be adjusted at a certain angle relative to the observation, so that the observer sees only the light diffused by the examined tissues.

A second type of instrument which is described at page 254 of the second reference above is an ophthalmoscope for the direct observation of the bottom of the eye without the use of a contact body. The problem of parasitic reflections is not completely eliminated because they might arise, for instance, at the surface of the cornea. In the second type of instrument, the optical lighting system is built so that an image of the light source is formed at the summit of the cornea, upon the axis of the observing beam. The image is brought there by a very small mirror, placed upon that axis of observation and upon the focal point of the illumination system. Thus, the parasitic reflections take an inverse path and are reflected by the mirror towards the source. The observation beam passes around the mirror, and being much larger than the mirror, it is only blocked in its central part by the mirror.

This construction of an intermediate image of the source considerably reduces the level of the parasitic light, although the illumination beam and the observation beam are coaxial.

A disadvantage of the first type of instrument is that it consists of two independent optical systems. For each examination, both systems must be manually adjusted, so that they aim at the same observation point at different angles. This task is difficult because the operator must be conscious of the fact that a contact body has to be handled. Furthermore, this adjustment must be repeated as often as different regions of the iris have to be examined.

The second type of instrument is limited only to observations of the bottom of the eye. Furthermore, the interruption of the center zone of the observation beam does not allow great depths of field to be achieved.

The first objective of the present invention is to provide an instrument which remedies the aforementioned disadvantages and allows illumination and observation of different regions of the eye together with greater depth and minimal aberration. The instrument is particularly suitable for use together with a contact body.

A second objective of the invention is the creation of an accessory for use after a diagnosis which enables the eye to be treated with a laser beam.

A third objective of the invention is to provide means which render the path of the treating beam visible within the eye in order to determine the plane of focussing and to prevent the beam from touching unwanted areas.

A fourth objective of the present invention is to provide means which allow the positioning of the focal plane of the treating beam upon the surface of the tissue or at a desired balance either behind it or in front of it.

The instrument for studying the eye according to the invention is characterized by providing optical elements which comprise means for forming optical illumination beams which issue from a light source. The beams consist of parallel rays whose axes are eccentric and parallel to the axis of the focusing lens and traverse said lens.

The device according to the invention offers the advantage of combining observation beams as well as illuminating beams in one optical system. Therefore, the need for separate regulation of two independent systems is eliminated.

Since the observation beam is coaxial with the optical axis of the instrument, an image having low aberration is produced.

The beams or beam emerging from the focusing lens or the eccentric illuminating rays exhibit a certain inclination relative to the axial observation beam. Thus, when a contact body is used under conditions of minimal aberration (i.e. the entrance plane is perpendicular to the axis of observation), no parasitic light distrubs the observations.

Other advantages of the instrument of the invention will be explained hereinbelow.

BRIEF DESCRIPTION OF THE DRAWING

FIGS. 4a and 4b are schematic views of another embodiment of the invention;

DETAILED DESCRIPTION

Figure 1:
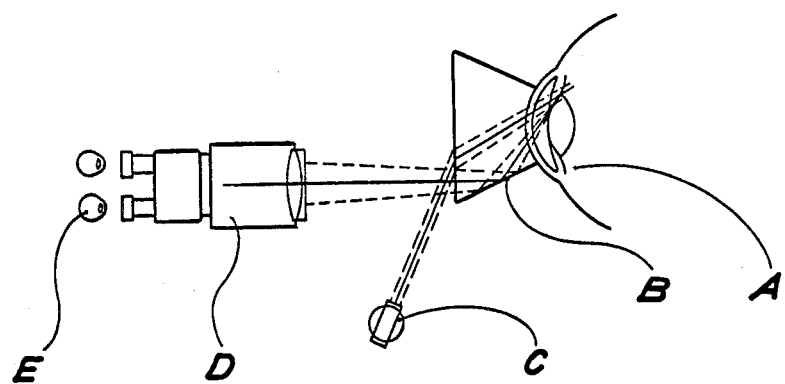
FIG. 1 is a pictorial view illustrating an observation instrument according to the prior art.
Figure 2:
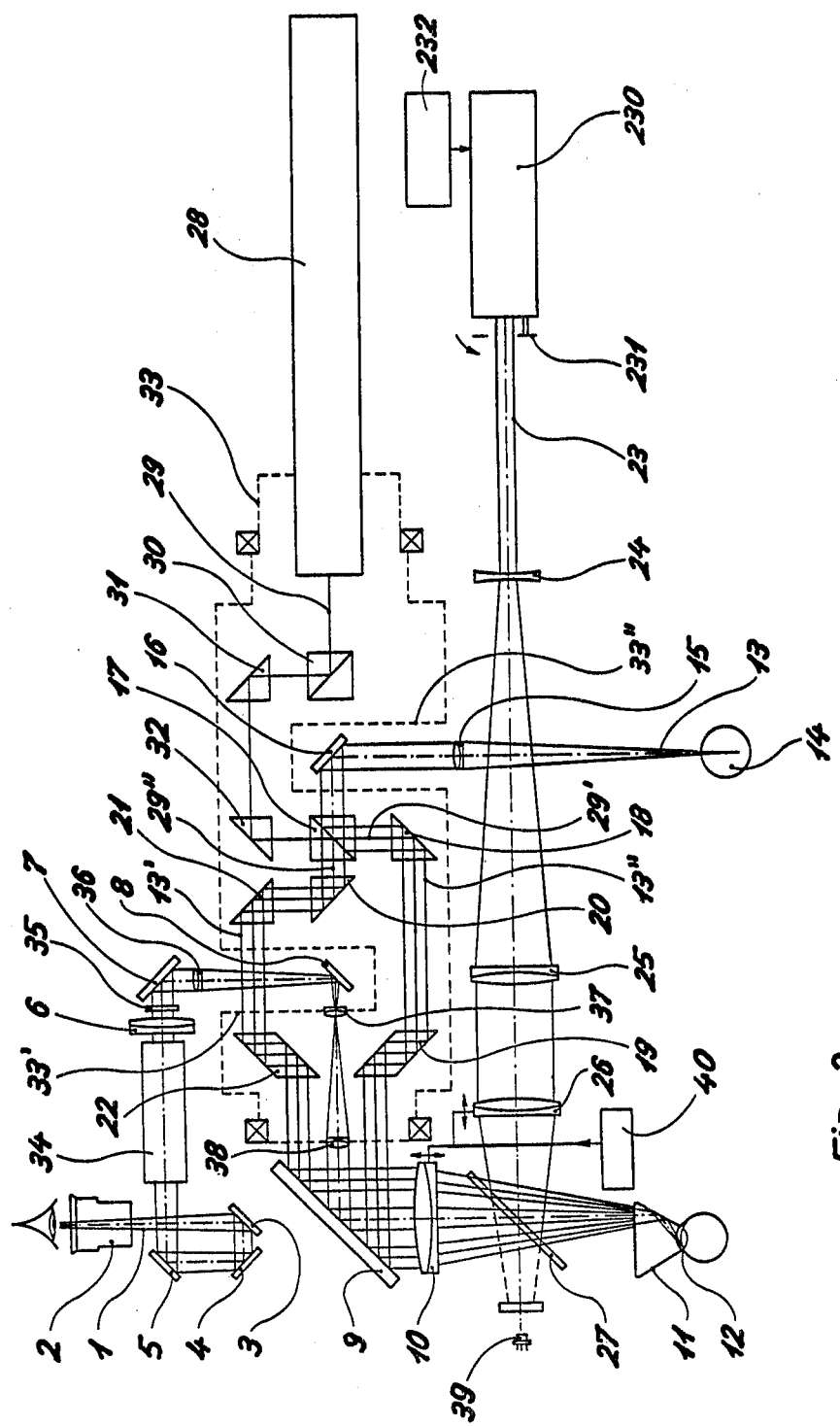
FIG. 2 is a schematic diagram illustrating an instrument according to the present invention.

The description of the invention is now set forth with respect to FIG. 2 which schematically shows one embodiment of the instrument according to the invention.

The optical observation beam is shown by zone 1. On issuing from a ocular 2, the beam 1 is successively reflected by mirrors 3, 4 and 5 until it reaches a converging lens 6, whose focus is the focus of the ocular 2. After passing through lens 6, the optical observation beam becomes a parallel beam and is reflected successively by the mirrors 7, 8 and 9 in order to be brought coaxially upon the focussing lens or objective 10. The optical beam is focussed by that last focussing lens 10 across a contact body 11 upon the zone or point of observation 12 of the eye of the patient. In the present case, the observation point 12 is the irido-cornean angle.

An optical illuminating beam 13 issues from block 14 which consists of a light source (incandescent lamp, arc light, discharge light), a condenser and a diaphragm (not shown). The illuminating beam 13 is forced to be parallel by a converging lens 15 whose focus is disposed in the plane of the diaphragm of block 14. The beam is then reflected by the mirror 16 and is split in the concrete sample shown by the beamsplitter 17 consisting, for example of prisms or a semitransparent mirror into two beams 13' and 13". After successive reflections by optical elements (prisms or mirrors) 18 and 19 for beam 13" and 20, 21 and for beam 13', the two parallel beams 13' and 13" are reflected by mirror 9 and arrive at the focussing lens 10. They are now parallel to the optical observing beam 1 and eccentric relative to the optical observing beam 1. The illuminating beams 13' and 13" are then focussed unto the focus of lens 10, in other words onto the observation point 12 where the image of the diaphragm of block 14 appears.

Some of the advantages of the instrument according to the invention are now set forth. The optical observing beam is an axial beam, thereby minimizing aberrations. The aperture of the observing beam may be chosen to be very small, allowing a great depth of field. The illuminating beam may be divided in any number of such beams, furnishing illumination under various angles. The angle of illumination may even be chosen by simply blacking out one or more illuminating beams. Illumination directly reaches the point of observation without need for regulating an independent system. This arrangement considerably simplifies the control work of the ophthalmologist during gonioscopic exams by aid of a contact body.

The illumination beams exhibit in their last path from the lens 10 an inclination relative to the observation beam. The beam does not include any parasitic rays reflected by the entering surface of the contact body except at certain particular positions of the contact body. In that case, it is sufficient to modify the position of the contact body or to modify the direction of the incident beam, as described herebelow.

The instrument according to the invention is not only useful for the observation and examination of the eye but also for the surgical treatment of the eye by means of laser-rays. One of the main applications of the instrument is the possibility of treating glaucoma surgically after observation and diagnosis by the physician.

The laser treatment-beam actuating the surgical operation is shown at 23. The laser treatment-beam may issue, for instance from a solid state laser at an impulse mode (in other words at Q-mode). The wave-length will be typically close to 1 micron. A Nd-YAG laser, for example, emits mainly at 1.06 mu. In contradistinction to the observing beam 1 where a great depth of field is desirable, the laser treatment-beam 23 in its desired surgical application should be at a maximal value due to physical laws, in order to produce large energy densities, localized in space. Therefore, the beam is enlarged by lens 24, rendered parallel by lens 25 and focussed by converging lens 26. The laser treatment-beam is superimposed upon the optical observation beam 1 by means of a reflecting surface 27. This surface 27 may consist of a mirror which intersects the optical path by rotation or translation, only at the moment when the laser is fired. Nevertheless, the reflecting surface 27 consists, preferably, of a lamella with an interference coating. It reflects a very weak band of waves around the laser treatment-wave; for example, the radiation of Nd-YAG being at 1.06 mu.

The axial position of the focussing point of the laser treatment-beam must be capable of very precise definition prior to its use. Thus, the regulation is accomplished with lens 10 as if it were lens 26. Lens 26 is, in fact, the image of lens 10 given by mirror 27, because both lenses are coupled by a device 40, preferably an electronically controlled device. All manual displacements of lens 10 are now transmitted to lens 26.

The electronically controlled device 40 allows the displacement of lenses 10 and 25 in the direction of the arrows shown in FIG. 2. The connection between lenses 10 and 26 is actuated by a motor, not shown, in FIG. 2 in order to improve clarity and comprehension of the illustration and is shown in dashed lines. For example, this motor may be a d.c. motor, because such motors react to precise displacement commands with good linearity. The system which commands the displacement of the lenses will not be described in detail because such command-circuits are well known in the art.

Considering the great depth of field of the observing beam 1, it is not possible to locate precisely by visual observation the position of the focus of lens 10 and consequently also the focus of lens 26.

A combined device aids in the exact determination of the focal plane of lens 10. A weak continual laser source 28, for example a He-Ne laser is used. The emitter laser beam 29 is directed across the reflecting surfaces (prisms or mirrors) 30, 31 and 32 towards the same beamsplitter 17, where it is divided and follows the same optical paths as the illuminating beams 13' and 13". The divided laser-beams 29' and 29" are focussed by lens 10 onto its focus.

Each of the incident beams produces a bright spot upon the tissue of the eye. The focal plane of lens 10, and consequently the plane of the path of lens 26 are located exactly on the surface of the tissue in the eye, while they coincide and superimpose with the bright spots observed by the ophthalmologist. The instrument allows an extremely sensitive adjustment of the focus of the treatment-beam 23 by choosing a maximal angle between the beams 29' and 29". The adjustment is done by referring to the desired aim or observation point 12, and this is accomplished, although the instrument allows a great depth of field.

When the first adjustment is completed, the axial position of the focal point of the laser treatment-beam relative to the surface to be treated must be modifiable as a function of certain parameters, which are mostly energy-related either in the front or in the rear of said surface. This axial shifting between the focal point of the treatment-beam and treated surface may be achieved, for example, by rotating the objectives 10 and 26. The electronic device 40 could, in that case, control the precision of the aforementioned shifting.

It is noticeable that the distance between the visible laser beams 29' and 29" when emerging from the focussing lens 10 is as large as the opening, limited by these beams for the laser treatment-beam 23. In fact, it is important that beam 23 be incapable of reaching or touching any other part of the eye but the one towards which it is directed. That is particularly true for the iris, which, due to its pigmentation, would be immediately damaged by high power laser-beams. Thus, the two beams 29' and 29" limit the laser beam 23 in one plane only because they are tangent to the external lateral surface envelope of the treatment laser. According to a non-limiting variant, the two lasers 29' and 29" form, with their axis, a tangent to the external lateral surface of laser-beam 23.

There are two solutions to this problem. One could multiply the number of beams 29 by successive splittings and thereby slowly envelope the conus that forms the power laser or, one could devise means to allow the visualization of the laser beam 23 in any plane which contains the optical axis.

The latter means will be illustrated. The combination of mirrors responsible for the splitting of the beams 13 and 29 is mounted in a tube 33 which may be turned around its axis, which is at the same time the optical axis of the system. It moves with the mirrors or prisms 17, 18, 19, 20, 21, 22, 30, 31 and 32. Mirror 9 is now a fixed mirror. The tube 33 contains radial apertures 33' and 33" in order to allow the observation beam 1 and the illuminating beams 13 to pass and enter the optical device transversally.

Thus, by turning tube 33, a rotation around the optical axis of the illuminating beams 13' and 13" and of sighting beams 29' and 29" is caused. Thus, it is possible to circumscribe and completely visualize the volume of space of the solid angle, occupied by the laser treatment-beam 23 prior to firing the same into the eye and thus to see whether it intercepts the iris. Furthermore, it is also possible to use the same instrument to prevent splitting or parasitics of the beam caused by the contact part or any other obstacle.

As mentioned before, tube 33 also offers the possibility to easily modify the direction of incidence of the illumination beams 13' and 13" and upon the observed zone in case that a particular position would cause direct reflection of part of the illumination into the observation beam 1. It is extremely easy to eliminate this inconvenience. But the axial rotation of tube 33 does not modify the control of aiming and setting of the focusing point and it has nothing to do with the observation beam 1, which by itself intersects only fixed mirrors.

Furthermore, it is easy to see that the split illumination beams 13' and 13" each undergo several pairs of reflections by the mirrors placed inside the movable tube. Thus, when beam 13 issues, for example from a slit, the orientation of the slit is conserved in its image in 12 for the entire rotation of tube 33 around its axis.

The particular geometry of the optical elements within the instrument are intended to fulfil three criteria; the patient must face the ophthalmologist, the eye of the patient must be situated within reach of the physician's hands, and the means of observation must furnish a convenient enlargement of the observed zone.

Other details of the construction, shown in FIG. 2 serve to enhance the performance of the instrument.

The rectangle 34, disposed along the optical path of the observation beam 1 denotes an image inverter which brings the image into correspondence with reality.

The rectangle 35 denotes a filter absorbing all parasitic radiation arising from the laser treatment-beam which might be reflected back into the observation beam.

The group of three convergent lenses or objectives 36, 37 and 38 forms an optical relay. The objective 37, located partly at the focus image of 36 and partly at focus object of 38 cooperates with objectives 36 and 38. This well know combination is utilized and also is used regarding the energy balance (conservation of light on a long parallel path) in order to reduce parasitic reflections by the contact body.

The detector 39 (a phototransistor, for instance) allows measurement and direct control of the temporal and energetic transmission characteristics of the laser treatment-beam. These measurements are made possible by the losses of reflection by the interference lamella 27.

Figure 3:
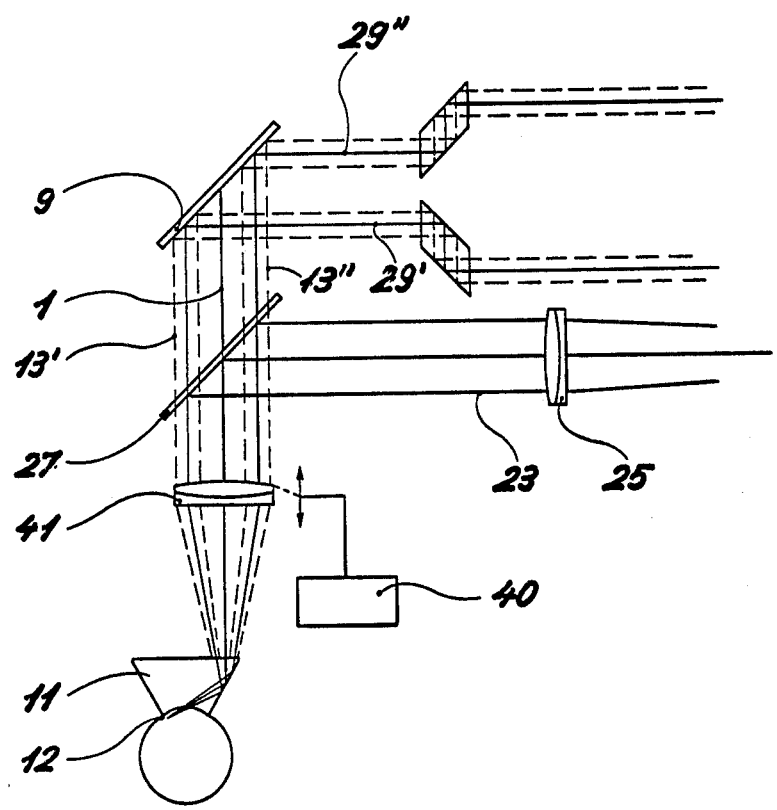
FIG. 3 is a schematic diagram of another embodiment of the invention of FIG. 2.

According to a detail of the embodiment shown in FIG. 3, which is another embodiment of the invention, the focussing lens 10 and the focussing lens 26 of the group of lenses which intercept the power laser beam 23 are constituted by one single lens 41. Lens 41 consists of a convergent lens, disposed in front of the contact body 11 and receives the parallel coherent light beams 29' and 29", the illuminating beams 13' and 13", the observation beam 1 and the power laser beam 23. According to the embodiment of FIG. 3, the power laser beam is transmitted to lens 41 by means of a reflecting surface 27.

The device may also be furnished with a system 400 (FIG. 4a) in order to set up the device by moving the lens 41, for instance. The system 400 may be formed of a manual displacement system driven by a micrometric screw.

Other embodiments, including replacing optical system including ocular 2 and allowing the physician to manually adjust the system could be used with the invention.

According to a preferred embodiment of the invention shown in FIG. 4a, the instrument may include a binocular system to prove the observer with a stereoscopic view.

For this effect, the ocular 2 is replaced by a binocular 200 allowing the observer to view observation beam 1' and 1", which allows binocular vision or a stereoscopic view of the image projected by lens 6. The relative effects of the reflecting surfaces 3, 4, 5, 7, 8 are, for example, unchanged because their dimensions are large enough to allow reflection and transmission of the two observation beams. The lenses 36, 37 and 38, on the contrary, are split in two in order to assure identical focussing of the observation beams. The system of lenses 10, 26 or 41 and the reflecting surface 27 remain unchanged. The binocular device will be described in FIG. 4a only for the case of FIG. 3, where the device consists of one single focussing lens 41 in order to simplify the illustration.

FIG. 4b represents the image of the illuminating beam 13, the image of the source of block 14 of the laser treatment-beam 23, and the binocular observation beams 1' and 1" at the level of the focussing lens 41 seen at the entering face 111 of the contact body. The binocular observation beams 1' and 1" preferably have their axes disposed longitudinally in a plane perpendicular to the plane which contains the longitudinal axis of the illuminating beam 13 and the optical axis 410 of lens 41. According to the embodiment of FIG. 4a, the instrument of the invention contains a single illumination beam 13 disposed at a fixed angle relative to the two binocular observation beams.

The reflecting surface 16, shown in FIG. 4a only shifts the beam along the longitudinal axis of beam 13, so that it avoids the splitting of the prism system 17, because the system of prisms reflects the intercepted beam 13. In order to prevent the observer from viewing parasitic beams caused by the reflection of the image of the illumination source 14 at the entering face 111 of the contact body, the image of the illumination source of block 14 and the image of the observation-pupils of beams 1' and 1" upon the entering face 111 of the contact body are separate. That occurs without regulating the contact body itself, as described before. This operation would require a new set-up by the command device 400 for the focussing lens 41. For that lens 15 allows the formation of the image of the source upon the entrance face 111 of the contact body and lens 15 comprises a group of simple lenses arranged in a conventional manner. Thus, set-up by the ophthalmologist necessitates nothing but slight displacement of the contact body 11 in order to compensate for slight erratic movements of the eyeball not inhibited by local anesthesis of the eye muscles. At that stage, all parasitic reflections of the image of the source of block 14 are practically eliminated by the split between the images of the source and the observation beams upon the entrance face 111 of the contact body.

The following is cited as a non-limited example of the present invention: The binocular is a binocular of "C" enlargement between 10 and 30, $10 \leq C \leq 30$, which range of enlargement enables the ophthalmologist to easily set up the examination. Thus the instrument, according to the invention, allows successively with the aid of only one means: observation of the anterior chamber of the eye or of any other part of the eye for a diagnosis, precise determination of the zone of impact of the focussed laser beam, direct observation of firing and of the trajectory of the laser beam and verification of the impact of said laser beam. In order to allow the physician control of the effect of each laser impulse, the device, according to the invention, is furnished with a system which regulates the position of the focussing point of the power laser beam relative to the observation point 12, defined by the superimposition of the focus points of the laser beams Helium-Neon, 29' and 29". For this effect, the device according to the invention is furnished with a command system 241, which moves the divergent lens 24 along its optical axis. The lens 24 is coupled to an attenuator 242 acting on the intensity of the power laser beam 23. As a non-limiting example, the attenuator consists of a polarizer and an analyzer of adjustable relative orientations. The command system 241 for moving lens 24 allows adjustment of the treated zone by displacing the focussing point of the beam relative to the tissue to be treated.

The aforesaid describes an instrument for treating various ophthalmological problems, such as glaucoma, by irridating the anterior chamber of the eye. The device may also be used for an iridectomy or for treatment of detachment of the retina. In the last case, though, a treatment beam 23 of a smaller diameter may be used by changing the lenses 25 or 24 into less or more diverging lenses respectively, which are of the same type and can be handled by the physician when mounted upon a turntable.

The device according to the invention is not limited only to the schematically illustrated examples of FIGS. 2, 3 and 4a but also includes devices which may have other geometric arrangements. The illumination beam 13 and the aiming beam 29 may be split not only in two but split any number of times.

Figure 5A:
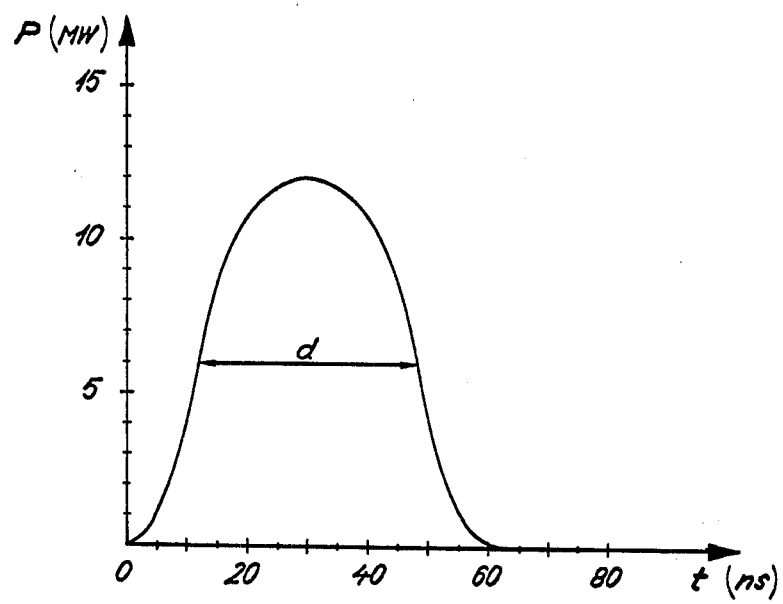
FIGS. 5a and 5b are waveforms relating to the invention.

As a non-limiting example like the one shown in FIG. 5a, the characteristics of emission of a laser beam for the treatment of glaucoma are the following for a wavelength near 1.06 mu:

the resonator operates in mode "TEMoo" and the luminous intensity distribution of the laser beam as a function of the distance from the optical axis is approximated by a Gauss-curve, the duration of the pulse at mid-strength is between 20 and 60 ns, the luminous energy of each laser pulse is between 50 and 400 millijoules and the luminous power at peak at emission is between 0.8 and 200 Mwatts.

The power density in the vicinity of the focal point lies between $2 \times 10^7$ and $2 \times 10^8$ W/cm$^2$, corresponding to an electrical field produced between $10^5$ and $5 \times 10^5$ V/cm. The latter is high enough to generate a dielectric rupture of the means of propagation and its ionisation. This ionisation is followed by a localized micro-explosion in the vicinity of the focussing point and by a pressure-wave or shockwave of spherical shape which is used for tearing the tissue to be treated and to form an aperture therein. The aperture produced by the shockwave caused by the focussing of the laserbeam has a stabilizing influence whereas apertures produced by volatilization of tissue by the influence of high temperatures only upon the tissue, caused by the focussing of a laser for protracted times at lower energies causes rapid scar formation.

Figure 5B:
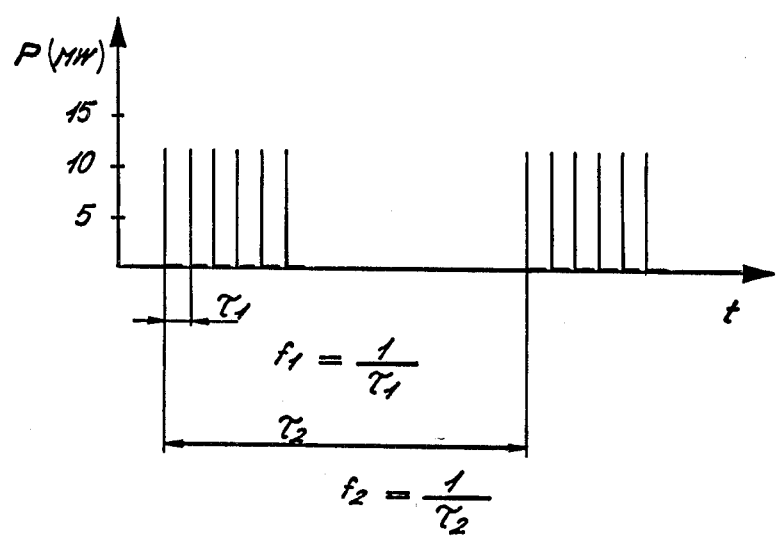

According to the impression of the physician, the emission may be applied in steps, see FIG. 5a, when the laser pulses have the aforecited characteristics or in groups of pulses for repetitive treatment, shown also in FIG. 5b. In fact, in that case, the crest of the luminous emission force may be diminished noticeably while the pulse repetition rate is kept constant. This pulse repetition rate $f_1$ is related to the characteristics of propagation of pressure waves within the aqueous liquid of the anterior chamber of the eye and is understood to be within a range of 50 kHz to 10 MHz. Periodic repetition of the same treatment, but by series of pulses at a frequency $f_2$, which is lower than 200 Hz allows less powerful pulses to be used for results comparable to those with progressive action. Such a treatment must consider the reestablishment of equilibrium conditions in the aqueous liquid of the eye.

For this effect, as shown in FIGS. 2 and 4a, the emission source of the power laser 230 contains a shutter 231 whose variable timing allows the treating physician to regulate the shutter and thereby the number of pulses received by the patient for a given treatment. The shutter, represented schematically by a mobile slotted disc may be operated as a conventional opto-electronic device. The pulse repetition rate may also be adjusted in relation to the demanded treatment by a command system, 232, which regulates the rate. The command system 232 is described, for example, in the U.S. Pat. No. 4,039,832, granted to the applicant.

Figure 6A:
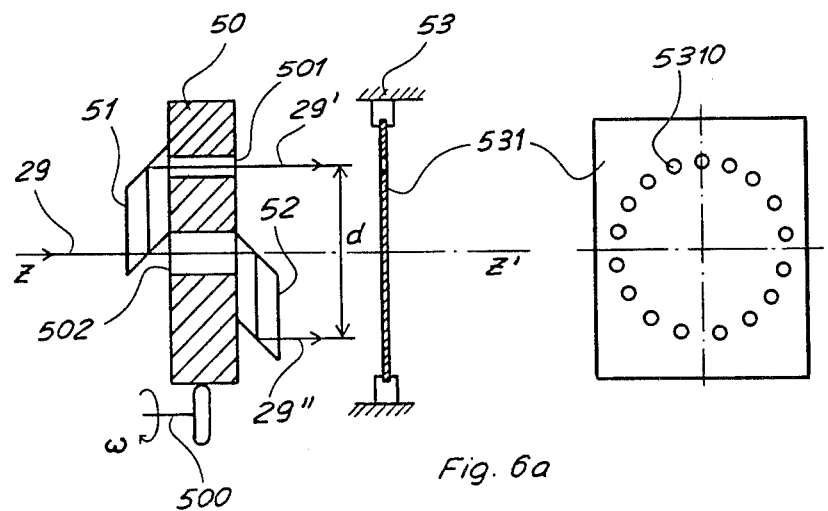
FIG. 6a is another embodiment of this invention.

According to the particular embodiment of the invention shown in FIG. 6a, the coherent visible light-beam 29 is generated by means of a particular system. This system for generating the envelope of the treatment laser beam 23 includes a rotating disc 50 whose axis of rotation coincides with the direction of propagation axis Z Z' of coherent visible light beam 29. A first and second prism with parallel faces 51 and 52 are substantially arranged along a diameter of disc 50. First and second prisms 51 and 52 function both as a lamella with parallel faces and allow the splitting of the coherent visible light beam 29 into two elementary parallel visible light beams 29' and 29''. Elementary parallel light beams are transmitted through bores 501 and 502 of disc 50. Elementary parallel light beams 29' and 29'' are distant from one another by a distance d substantially equal to the diameter of treatment laser beam 23.

Figure 6B:
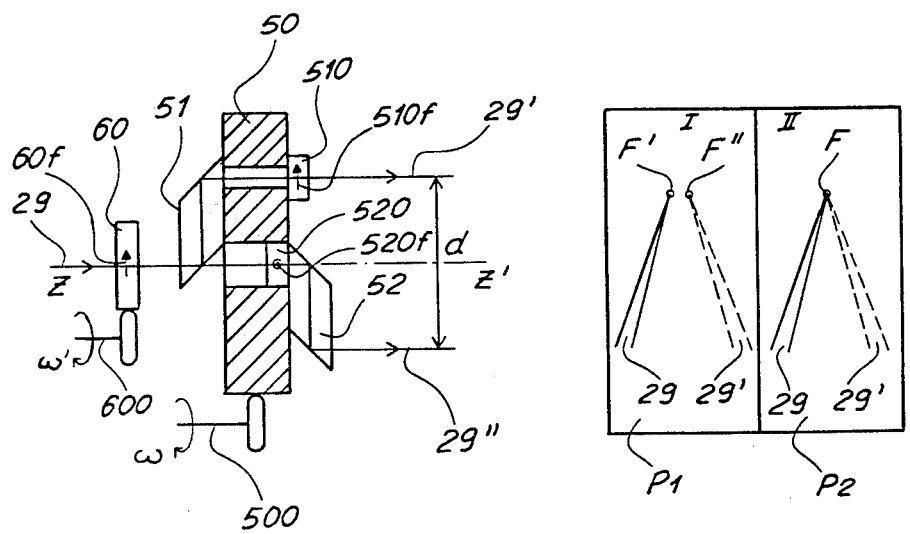
FIG. 6b is an alternative embodiment of the modulator of this invention.

Prism 51 and 52, as shown in FIGS. 6a and 6b, play the same function as that of mirrors 17, 18, 32 according to FIGS. 2 and 4a. The rotation of disc 50, which, for example, is rotated at an angular speed $\omega$ by the friction of a rotating spindle 500 allows the motion of elementary parallel visible light beam 29' and 29'' to be tangential to a guiding line of treatment laser beam 23 thereby generating the envelope of the latter. The system for generating the envelope further includes a modulator 53 which is a system for modulating the light intensity of the elementary visible light beams 29' and 29''. This modulator is preferably a binary modulator type allowing the simultaneous transmission and cut off of the coherent elementary visible light beam 29' and 29'' respectively.

According to the embodiment of FIG. 6a, the modulator 53 comprises a fixed screen 531 provided with a plurality of bores 5310. The diameter of bores 5310 is substantially equal or slightly greater than the diameter of elementary coherent visible light beams 29' and 29''. Bores 5310 are arranged according to a circle which is the locus of the elementary visible light beams 29', 29'' which impinges on screen 531 when disc 50 is rotated. Bores 5310 are distant from one another along an arc of a distance substantially equal to the diameter of bores 5310. Along a diameter, two opposite points of the locus of impingements comprise a bore or an absence of a bore.

FIG. 6b shows another embodiment of the modulator. According to FIG. 6b, modulator 53 comprises a rotating polarizer 60. Polarizer 60 rotates at an angular speed $\omega'$ around the Z Z' axis of coherent visible laser light beam 29 by friction with a rotating spindle 600. Polarizer 60 transmits the coherent light laser beam 29 as polarized light. The direction of polarization represented by arrow 60f varies at the angular speed $\omega'$ in a plane perpendicular to axis Z Z'. Modulator 53 further comprises a first and second analyzer 510 and 520 rigidly locked with disc 50. Analyser 510 and 520 each transmit elementary coherent light beams 29' and 29'' as polarized light according to the two directions represented by 510f and 520f, which are substantially perpendicular.

In such case, the modulation of light intensity is performed at a frequency substantially proportional to the relative rotation speed $\omega' - \omega$ of disc 50 and polarizer 60.

The two above embodiments of the modulator allow the detection in operation by the doctor of the coincidence at their common focussing point of elementary coherent visible light-beams 29' and 29'' according to the following mode of operation as shown at I and II FIG. 6b.

The intersection of elementary coherent visible light beam 29' and 29'' by a plane P1 distinct from focal plane of focussing lens 41, as shown at I, gives rise to the existence of two images F' and F''. These images formed by the intersection of plane P1 and beams 29' and 29'' flicker at a frequency $F_c$ in relation with the speed of rotation $\omega$ of disc 50. The relative shifting of plane P1 to P2 for the obtention of an intersection at the common focussing point of beams 29' and 29'' as shown at II gives rise to a single image at F, which is the superimposition of beams 29' and 29'' at their common focussing point. Image F is free from flickering.

The embodiment of FIG. 6b allows the selection of rotation speeds $\omega$ and $\omega'$ of disc 50 and polarizer 60 to be optimalized so that in operation the doctor may have a maximum detection accuracy and sensitivity. As a matter of fact, rotation speed $\omega$ may substantially be chosen in relation with the mean time for the response movement of the doctor's hand to maintain the contact glass on the eyeball of the patient. During that time, the elementary coherent visible light laser beams 29' and 29'' are deemed to run half a circumference of the locus of impingements and allows the doctor to check the absence of impingement of elementary coherent visible light beams along their optical path and, as a consequence, the same for treatment laser beam 23. The rotation speed $\omega'$ then can be chosen by the doctor in relation with the above-mentioned speed of rotation $\omega$ in order to optimalize the accuracy and sensitivity of detection.

Figure 6C:
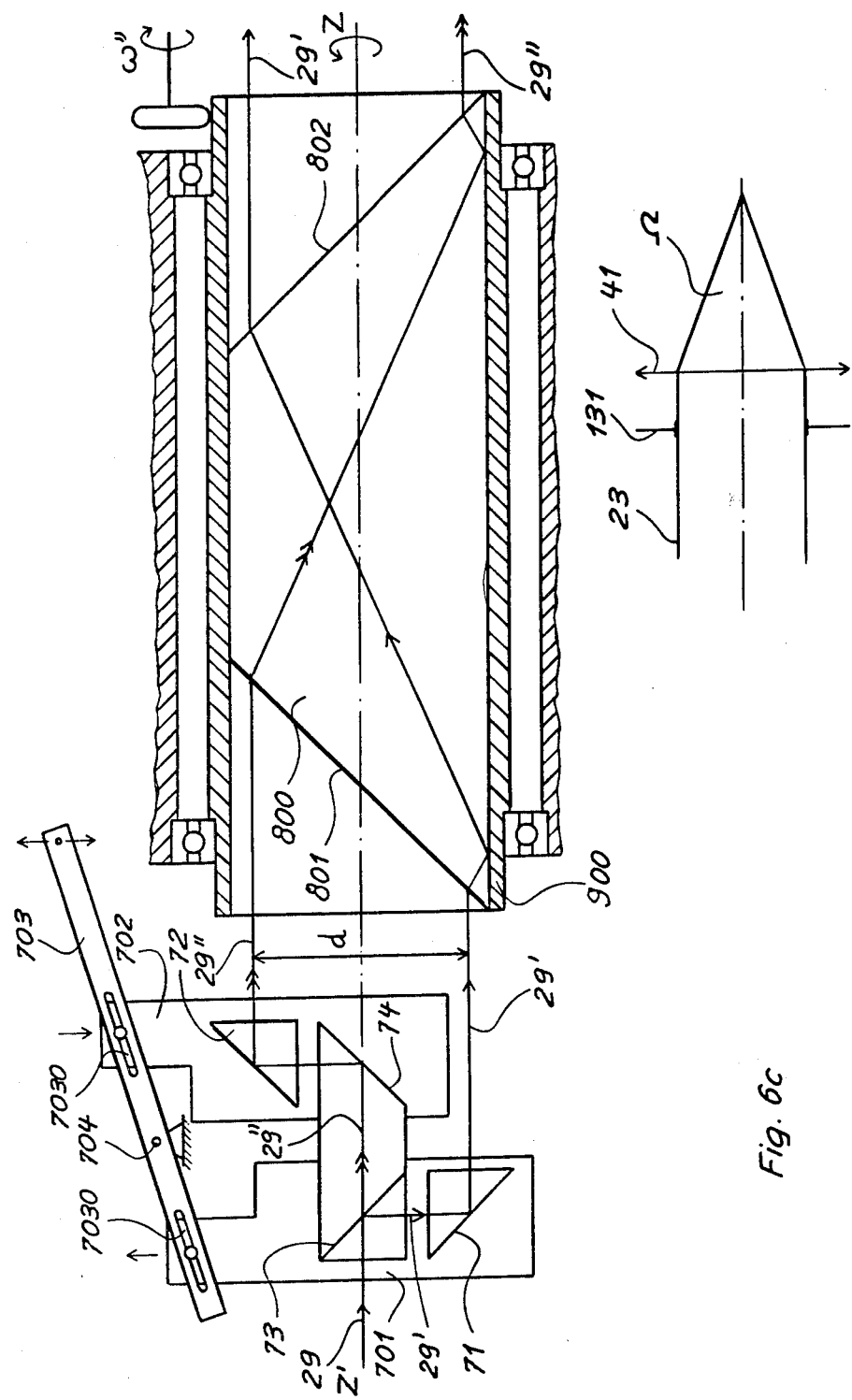
FIG. 6c is still another embodiment of a portion of this invention.

According to another embodiment shown in FIG. 6c, the focussing lens 41 for the treatment laser beam 23 is coupled with an adjustable diaphragm 131. For example, diaphragm 131 is constituted by an iris diaphragm. This diaphragm allows the focussing solid angle $\Omega$ of treatment laser beam to be selected without any modification of the focal length of the focussing lens. This selection is done according to the doctor's diagnosis. In such a case, the system for generating the envelope of the treatment laser beam is changed as shown in FIG. 6c so that elementary coherent visible light beams 29' and 29'' remain representative of the treatment laser beam envelope whichever the aperture of diaphragm 131 and corresponding treatment laser beam diameter may be. Prisms with parallel faces 51 and 52 are replaced by mirrors 71 and 72 respectively arranged on a movable frame 701 and 702. Mirrors 71 and 72 are respectively coupled with a partial reflecting mirror 73 and a mirror 74. Partial reflecting mirror 73 and mirror 74 are coupled face to face and allow the splitting of coherent visible light-beam 29 into two beams 29' and 29'', both perpendicular to beam 29. Mirrors 71 and 72 are movable in translation according to that direction perpendicular to beam 29. For this purpose, mirrors 71 and 72 are rigidly locked with movable frame 701 and 702.

The symetrical translation of movable frames 701 and 702 along a direction perpendicular to visible laser beam 29 axis Z Z' is performed by means of a lever 703 provided with a slide 7030. Lever 703 is movable around a fixed point 704. The elementary coherent visible beams 29' and 29" are reflected in a direction parallel to that of visible beam 29 by mirrors 71 and 72. Displacement of lever 703 performs the symetrical increase or decrease of the distance d separating coherent visible light beams 29' and 29". The system for generating the envelope of the treatment laser beam comprises a prism 800 whose inclined faces 801 and 802 function respectively as input and output faces of elementary coherent visible light radiation 29' and 29". Prism 800 is rigidly locked in a rotating frame 900. Frame 900 rotates with an angular speed $\omega''$. A rotation of prism 800 of an angle $\alpha$ according to a plane perpendicular to the direction of beams 29' and 29" produces a similar rotation of these beams downstream of the inclined output face 802 of an angle $2\alpha$ according to a parallel plane. The device for rotating prism 800 and movable frame 900 are not shown in FIG. 6c in order to simplify the figure since this kind of device is well known to one skilled in the art.

A modulator 53 constituted by a screen provided with bores as shown in FIG. 6a and receiving beams 29' and 29" downstream of the inclined face 802, or a modulator including a polarizer 60 together with analysers 510, 520 can either be used with this kind of system for generating the envelope of treatment laser beam.

Variations and modifications can, of course, be made without departing from the spirit and scope of the invention.

What is claimed is:

1. Apparatus for treating the eye with a laser beam to effect ophthalmological surgery on said eye, said apparatus comprising an optical system for observing and treating the eye, means to produce a treatment laser beam having an axis, means for employing said optical system to observe the area of the eye to be treated and to treat said eye with said laser beam, means to produce two elementary beams of visible coherent light rotating about the axis of said treatment laser beam in such a way to generate its envelope, means to modulate the light intensity of said elementary beams, said optical system comprising a focusing lens for directing the treatment laser beam on the area of the eye to be treated and means to adjust said optical system to ensure that the treatment laser beam is focused on the plane of treatment and that said treatment laser beam does not contact untreated portions of the eye prior to energizing said treatment laser beam for surgically treating the eye, said means to adjust being utilized when a light spot formed by the elementary beams in the plane of the focus of said focusing lens is flickering.

2. Apparatus for treating the eye as claimed in claim 1, wherein said means to modulate the light intensity of said elementary beams comprises means to periodically interrupt the transmission of one of the elementary beams while the other is transmitted.

3. Apparatus for treating the eye as claimed in claim 1, wherein said means to adjust comprises means to control the axial position of said focusing lens.

4. Apparatus for treating the eye as claimed in claim 1, further comprising means to adjust the relative position of the apparatus for treating the eye with respect to the eye.

5. Apparatus for treating the eye as claimed in claim 1, further comprising a system for generating the envelope of said treatment laser beam by using a coherent visible light beam having an axis of propagation, said system comprising:
a rotating disc whose axis of rotation coincides with the direction of said axis of propagation of said coherent visible light-beam,
first and second prisms with parallel faces substantially arranged along the diameter of said rotating disc, said first and second prisms allowing the splitting of said coherent visible light-beam into two elementary parallel visible light-beams distant from one another by a distance substantially equal to the diameter of said treatment laser beam.

* * * * *